United States Patent
Thornton (10) Patent No.: US 11,369,035 B2
(45) Date of Patent: Jun. 21, 2022

(54) DATA CENTRE

(71) Applicant: Bripco (UK) Limited, Cheltenham (GB)

(72) Inventor: William Thornton, Cheltenham (GB)

(73) Assignee: Bripco (UK) Limited, Cheltenham (GB)

( * ) Notice: Subject to any disclaimer, the term of this patent is extended or adjusted under 35 U.S.C. 154(b) by 0 days.

(21) Appl. No.: 16/475,799

(22) PCT Filed: Jan. 16, 2018

(86) PCT No.: PCT/EP2018/050953
§ 371 (c)(1),
(2) Date: Jul. 3, 2019

(87) PCT Pub. No.: WO2018/130705
PCT Pub. Date: Jul. 19, 2018

(65) Prior Publication Data
US 2020/0384050 A1 Dec. 10, 2020

(30) Foreign Application Priority Data
Jan. 16, 2017 (GB) ..................................... 1700736

(51) Int. Cl.
*H05K 7/20* (2006.01)
*B01D 11/02* (2006.01)
(Continued)

(52) U.S. Cl.
CPC .................. *H05K 7/20* (2013.01); *A23L 5/23* (2016.08); *A23L 5/30* (2016.08); *A61K 36/185* (2013.01);
(Continued)

(58) Field of Classification Search
None
See application file for complete search history.

(56) References Cited

U.S. PATENT DOCUMENTS 8,514,572 B2 * 8/2013 Rogers ...................... E04H 5/02
361/695

FOREIGN PATENT DOCUMENTS

GB 2120378 A 11/1983
JP 2010270496 A 12/2010
(Continued)

OTHER PUBLICATIONS

Notification of Transmittal of the International Preliminary Report of Patentability, International Application No. PCT/EP2018/050953, dated Apr. 8, 2019.
(Continued)

*Primary Examiner* — Mukundbhai G Patel
(74) *Attorney, Agent, or Firm* — Carlos A. Fisher; Stout, Uxa & Buyan, LLP (57) ABSTRACT

A data centre (10) includes one or more controllable air circulation systems (e.g. air optimiser (11)), one or more cold aisles (15) and/or one or more hot aisles (16), one or more rows of racks (14), the data centre being so arranged that in use cooling air (18) passes, under the control of the one or more controllable air circulation systems, from a cold aisle (15) through the racks (14) and/or through the racks (14) to a hot aisle (16). An access door (20), which provides access to at least one of the aisles, is movable between an open position allowing personnel access to the aisle and a closed position. The door (20) has an aperture (25) in which is provided a controllable air intake arrangement, for example comprising a vent (17) in the form of multiple vertically extending rotatable blades (28). The width (24) of the door is wider than the width (26) of the aisle associated with the door (20), so that the width of the aperture (25) may be larger than or substantially equal to the width (26) of the aisle. Air-flow into the aisle may therefore be subjected to
(Continued)

less of a constriction than if the door (20) and aperture (25) were narrower.

21 Claims, 7 Drawing Sheets

(51) Int. Cl.
    *A61K 36/21*        (2006.01)
    *A61K 36/185*     (2006.01)
    *A23L 5/30*        (2016.01)
    *A23L 5/20*        (2016.01)
    *E06B 7/084*      (2006.01)

(52) U.S. Cl.
    CPC .......... *A61K 36/21* (2013.01); *B01D 11/0288* (2013.01); *E06B 7/084* (2013.01); *A61K 2236/19* (2013.01); *A61K 2236/333* (2013.01); *A61K 2236/51* (2013.01); *A61K 2236/53* (2013.01); *B01D 11/0257* (2013.01)

(56) References Cited

FOREIGN PATENT DOCUMENTS

| JP | 2011089317 A | 5/2011 |
| WO | 2010139921 A1 | 12/2010 |
| WO | 2016207323 A1 | 12/2016 |

OTHER PUBLICATIONS

UK Search Report Application No. GB1700736.0, dated Apr. 10, 2017.
PCT Written Opinion of the International Searching Authority, International Application No. PCT/EP2018/050953, dated Jul. 19, 2018.
PCT International Search Report, International Application No. PCT/EP2018/050953, dated Apr. 25, 2018.

\* cited by examiner

DATA CENTRE

BACKGROUND OF THE INVENTION

The present invention concerns data centres, a method of cooling equipment in a data centre and also subject matter ancillary thereto. More particularly, but not exclusively, this invention concerns data centre buildings having a hot aisle/cold aisle configuration and including at least one door for an aisle, wherein the door includes a controllable air intake arrangement accommodated in an aperture of the door. The invention also concerns such a door when provided by itself, a method of replacing a part of the controllable air intake arrangement of such a door, and a kit of parts for constructing a part of a data centre.

WO2010139921 (corresponding to International Patent Application No PCT/GB2010/000759) discloses a data centre building having a hot aisle/cold aisle configuration and including a vented door for each cold aisle. The cooling of the data centre of WO2010139921 is effected by supplying cooling air under a regulated air pressure regime. Each vented door includes a controllable air intake arrangement accommodated in an aperture of the door, which allows control of the flow of air through the door, when in its closed position. The provision of a door, even vented, in the manner disclosed in WO2010139921 risks disrupting airflows and leading to localised increase in air velocity that might adversely affect operation. Thus, whilst WO2010139921 describes a method of cooling a data centre that is able to achieve very high efficiencies, it may be that further efficiencies and/or improvements are achievable.

The present invention seeks to provide an improved data centre and/or an improved method of, or means for, cooling a data centre. Additionally or alternatively, the invention seeks to provide a data centre and/or a method of, or means for, cooling a data centre that mitigates one or more of the above mentioned disadvantages.

SUMMARY OF THE INVENTION

The present invention provides a data centre including one or more cold aisles and/or one or more hot aisles, and an access door providing access to at least one of the aisles, the door having an aperture in which is accommodated a controllable air intake arrangement. The door is movable between an open position allowing personnel access to the aisle and a closed position. In use of a data centre according to embodiments of the invention, cooling air flows via the doorway associated with the door, into or from the aisle when the door is in its closed position and the flow of air through the doorway, when the door is in its closed position, is controllable by means of the controllable air intake. In accordance with the present invention, the width of the door is wider than the width of the aisle. Given that the aisle will typically have a width that is substantially constant along its length, the door will therefore be wider than it needs to be in order to permit personnel access into/from the aisle. Indeed, having a door that is wider than the aisle will mean that in use the racks either side of the aisle will typically intrude into the doorway that is present when the door is open. However, in embodiments of the present invention, the concept of having a door that is wider than the aisle enables the aperture of the door to have a width that is larger than or substantially equal to the width of the aisle. This may enable the flow of air between the door (when closed, but with the air intake arrangement being fully open, for example) to be smoother as a result of the aperture having a width (and, for example, an effective cross-sectional area) closer to that of the aisle than would be possible with a door that has the same width as the aisle or narrower. The use of narrower vented doors (as proposed in WO2010139921 for example) may under certain operating conditions give rise to uneven distribution of cooling air along a cold aisle, which may cause certain servers to demand more cooling than others in the aisle and/or giving rise to "hot-spots" in the cold aisle (i.e. undesirable localised regions of air that is hotter than other regions in the aisle). For example, the body of such a narrow door (that is, the part of the door that is not the aperture) can effectively shield IT equipment from cooling air flowing through the aperture, especially at higher rates of airflow (in other words, fast flowing air bypasses IT equipment adjacent to the door and only spreads throughout the cross-section of the aisle some distance from the door). Given that it is important to ensure that the cooling air supplied to a given cold aisle satisfies the demand of all IT equipment in that aisle, more air may need to be supplied than is in theory necessary. This could potentially lead to inefficiencies, under certain conditions. It will now be appreciated therefore that, in embodiments of the present invention, the provision of an unusually wide door for the aisle may enable better and/or more efficient cooling of the IT equipment in the racks as compared to the same set-up but with a standard width door (i.e. a door that is substantially the same width or narrower than the aisle).

In a case where the aisle has different widths along its length or height, the width of the aisle may be defined as the average width (averaged over the height of the door) of the aisle which is the lowest width for all cross-sections of the aisle at any distance between 0.2 m from the door when closed to 2.4 m from the door. In a case where the door (or its aperture(s)) has different widths along its height, the width may be defined as the area taken up by the door (or its aperture(s)) divided by its greatest height as measured in a vertical direction. In certain embodiments of the present invention, there may still be benefit achievable even when the aperture of the door has a width that is less than the width of the aisle.

The data centre when fully installed and operational will typically include one or more controllable air circulation systems. It may be that the controllable air intake arrangement in the aperture of a door forms part of such a controllable air circulation system.

The data centre when fully installed and operational will typically include rows of racks arranged parallel to at least one of the aisles. In use, cooling air may then be caused to pass, under the control of the one or more controllable air circulation systems, from a cold aisle through the racks and/or through the racks to a hot aisle.

The door may have more than one aperture in each of which one or more controllable air intake arrangements are accommodated. Such a configuration may equally be considered as one aperture divided into sub-apertures with a single controllable air intake arrangement that spans all such sub-apertures.

The air intake arrangement may be movable to and from a fully open position. The air intake arrangement may be movable to and from a fully open position, a partially open position, and a closed position. The closed position may be such that some flow of air is permitted through the aperture. (It is not necessary in all embodiments of the invention for the air intake arrangement, when fully closed, to provide an airtight barrier which prevents any flow of air through the aperture.) The air intake arrangement may be arranged to move so as to progressively enlarge or progressively reduce the effective cross-sectional area of the aperture in the door. It may be that the air intake arrangement is configured to be movable to any one of at least five different positions, each position corresponding to a different level of openness. It will be appreciated that having a greater number of different positions, each corresponding to a different effective cross-sectional area of the aperture, of the air intake arrangement permits finer control of the air-flow through the door and into the aisle.

It is preferred that the width of the aperture is larger than, or substantially equal to, the width of the aisle. The width of the aperture, and the arrangement of the air intake arrangement when in its most open configuration, may be such that the air flowing through the aperture does not experience any rapid pressure change or significant change in velocity as it passes through the aperture. In this context, a rapid pressure change or a significant change in velocity is one that makes a significant difference to the supply of cooling air to the racks immediately next to the door. If the air is caused to travel faster immediately after it passes through the door, hot-spots may develop near the vertical edges of the door. Embodiments of the present invention are able to reduce the risk of such hot-spots developing.

The controllable air intake arrangement accommodated in the aperture of the door may comprise one or more controllable vents. Thus, in an embodiment of the invention, the access door into the data room has a controllable vent, so that the door has a dual function. It will be appreciated that the air flow regime of the building is arranged to function with all such doors normally being closed. Thus, the doors are arranged to be normally closed, for example only being opened when personnel access is required. The door arrangement may be located on the end of a cold aisle. The door arrangement may be located on the end of a hot aisle, in which case it will be appreciated that, in use, the air that passes via the door will typically have been heated by rack-mountable electronic components in the racks.

It may be that the access door is one or multiple such doors, each door providing access to a respective aisle. The one or more access doors may each be associated with a cold aisle. There may be provided a cold air supply region for transporting, under the control of the one or more air circulation systems, cooling air, above the floor, via respective access doors to the respective cold aisles. The cold air supply region may have a height greater than 1.5 m above the floor, possibly higher than 2 m. In some cases, the cold air supply region may have a height greater than 3 m. The cold air supply region may be in the form of an air supply corridor. The air supply corridor may also function also as a personnel access corridor. The air supply corridor may have a height greater than 1.5 m above the floor, for at least 90% of its length. The air supply corridor may have a large cross-sectional area, namely an area greater than 2 $m^2$, and preferably greater than 3 $m^2$. The air supply corridor may have such a large cross-sectional area for at least 90% of its length. The hot and cold aisles may each have cross-sectional area greater than 2 $m^2$, and possibly greater than 3 $m^2$. The air supply corridor is preferably entirely located above floor-level.

In data centres of the prior art it is common to provide under-floor air ducts. Certain embodiments of the present invention remove the need for such under floor ducts. There is therefore no need to have a high raised floor in embodiments of the present invention. The upper surface of the floor may be less than 500 mm above the base of the building, for example. Better use may therefore be made of the vertical space available in a building of a given height. The height of buildings may for example be limited if the buildings are assembled off-site and transported via road or rail networks in a part-assembled or fully assembled state. Additionally, or alternatively, the under-floor space may be utilised for functions other than air-ducts. For example, cables or other services may be routed under-floor.

Preferably, the data centre building is so arranged that in use air flows along a path from one or more air circulation systems via a corridor to/from at least one of the cold aisles, such that the air flow is substantially horizontal for the entire path. The path of air-flow is preferably entirely above floor level. The path of the air-flow may pass along at least part of a corridor, separate from both (a) each of the one or more cold aisles and (b) each of the one or more hot aisles, the corridor facilitating access from outside the building to one of the rack storage areas. It may for example be that a corridor together with at least one of (a) one or more cold aisles and (b) one or more hot aisles, provide personnel access to the racks, during operation of the data centre. It may be that the aforementioned door (or doors) separates an aisle from such a corridor. The one or more corridors via which air (whether or not heated by IT equipment in the racks) flows may extend in a generally horizontal direction for at least 90% of their length and preferably extend only in a generally horizontal direction for substantially their entire length. Thus, in an embodiment of the invention, an over-floor corridor may act as a cooling air duct. By using an over-floor corridor as a cooling duct, high rates of supply of air may be achieved whilst making efficient use of the space within the volume of the building.

The hot or cold aisles may each be positioned between two adjacent rows of racks. The hot or cold aisles may extend parallel to a row of racks. There may be a plurality (two or more) of cold aisles. There may be a plurality (two or more) of hot aisles. It may be that there are two or more cold aisles and two or more hot aisles, the aisles alternating between cold aisle and hot aisle. The data centre building may be so arranged that a plurality of cold aisles are interleaved between at least three hot aisles. The aisles may be substantially straight along their length.

It will be appreciated that a "cold aisle" may be "cold" in the sense that it is upstream of the rack storage area in the direction of flow of cooling air, in use. It will also be appreciated that a "hot aisle" may be "hot" in the sense that it is downstream of the rack storage area in the direction of flow of air from the racks that has, in use, been heated by IT components in the racks. The hot aisle may be hot in the sense that the temperature in the hot aisle is, once a steady state has been achieved during operation, typically higher than the temperature in the cold aisle.

It may be that each cold aisle has an access door associated with it. The cold aisle may be permanently closed at the opposite end. The cold aisle may be encapsulated such that air entering the cold aisle via the door and only leave, in use, via the racks. It may be that each hot aisle has an access door associated with it. Such an access door (for a hot aisle) may, or may not, be provided with a controllable air intake arrangement, as described herein. It may be that each hot aisle has at least one freely vented end that allows air to leave the hot aisle. It may be that each hot aisle has at least one end which is permanently closed, for example with a blanking panel.

As mentioned above, the door may comprise a controllable vent. The vent may be moveable between an open position thus allowing air to pass via the vent and a closed position. When in the closed position, airflow via the vent (controllable air intake) may be restricted (possibly substantially prevented). The controllable air intake arrangement may comprise a line of parallel spaced-apart blades arranged for rotation about their respective axes, such that the air intake arrangement may be moved between closed and open positions by means of rotation of the blades. For example, the controllable air intake arrangement may comprise a row of vertical blades arranged for rotation about a vertical axis.

The blades may comprise at least one pair of adjacent blades that are arranged to rotate simultaneously in opposite directions. The blades are preferably arranged to rotate together to effect control of the flow of air through the vent. There may be two or more motors to move the blades. There are preferably six or more blades. The blades preferably extend across more than 70%, possibly more than 75%, of the width of the door. The blades preferably extend across more than 80%, possibly more than 85%, of the height of the door. The effective open area when the vent is fully open may be greater than 1.5 m², possibly greater than 2.0 m². The vent is preferably arranged such that in the event of a failure the vent would fail "open".

The blades may be provided as two or more rows of vertical blades stacked one row on top of another. A horizontal bar may separate each adjacent pair of rows of blades. A horizontal bar may, in any case, be provided to assist in supporting one or more of the blades, for example holding the blades in position. Such a horizontal bar, in either case, may comprise bearings that assist in guiding the rotational movement of the blades. The horizontal bar may extend horizontally, for example from one side of the aperture to the opposite side. The horizontal bar and/or door may be provided with fixings that are configured to enable the bar to be mounted across the aperture. The bar may be configured so that one blade may be removed without the need to remove other blades. The bar may be in the form of a multi-section bar, so that one or more sections of the bar may be removed to facilitate maintenance and/or removal of one or more of the blades. The bar may divide one aperture into two sub-apertures. The bar may be vertically positioned between the top and bottom of the aperture, for example in the region between 20% and 80% of the height of the aperture. The bar may be vertically positioned approximately midway between the top and bottom of the aperture, for example in the region between 40% and 60% of the height of the aperture. The provision of a bar to support the blades may be of particular advantage when the blades are relatively tall. The blades may for example extend across more than 80% of the height of the door, and may extend from the bottom of the aperture to the top of the aperture, which may therefore span a distance of more than 2 m, possibly more than 2.4 m and in some cases more than 2.5 m.

The door may comprise at least one motor for moving the controllable air intake between an open position thus allowing air to pass via the air intake and a closed position. The at least one motor is preferably arranged so that the amount of airflow through the door may be adjusted between three or more levels. The level of adjustment possible may be substantially continuous as between the fully closed and fully open positions. The door arrangement may be arranged to receive a control signal for controlling the operation of the at least one motor. The control signal is preferably set in dependence on measured characteristics of the air in or immediately outside the building.

Aisles in the data centre will typically be 1000 mm wide or wider, for example at least 1200 mm. It may be that the cold aisles are of this width, but that the hot aisles are narrower. (In some embodiments, it may be that the hot aisles are not designed for routine personnel access.) The present invention has particular application with large doors having large apertures, as compared to aisle widths of a conventional size. The door (excluding its frame, if any) may have a width of greater than 1200 mm, preferably greater than 1300 mm and possibly greater than 1350 mm. The door may have a width of greater than 110% the width of the aisle. The aperture may have a width of greater than 1,100 mm, preferably greater than 1,150 mm and possibly about 1.2 m or more.

The one or more air circulation systems may comprise one or more fans. The fans may be arranged to push air through the building. Each fan may be sufficiently large to generate an air flow of at least 0.5 m³s⁻¹. Each fan is preferably sufficiently large to generate an air flow of at least 1 m³s⁻¹, and more preferably at least 5 m³s⁻¹. Together the one or more air circulation systems may have sufficient capacity to generate an air flow of at least 5 m³s⁻¹, and more preferably at least 10 m³s⁻¹. There may be five or more fans. For example, ten or more fans may be provided, such fans collectively being able to generate an airflow of at least 50 m³s⁻¹. There may be one or more exhausts arranged to allow for air to be exhausted from the data centre. The exhausts may be provided as passive exhausts, in that the exhausts do not themselves assist extraction of air from the building. The exhausts may include one or more controllable vents.

The one or more controllable air circulation systems may form part of a single air cooling system with built in redundancy for ensuring continued operation of the data centre building in the event of failure of one of the parts of the air cooling system. The single air cooling system may be in the form of a separate module. The single air cooling system may for example comprise a multiplicity of fans including at least one fan more than necessary (at least N+1 redundancy). The air cooling system may include a mechanical cooling unit, for example utilising a refrigerant-based cooling method, (possibly one only or possibly two for the sake of redundancy). The mechanical cooling unit may for example comprise an air conditioning unit having DX (direct expansion) refrigeration coils. The air cooling system may include a chilled water air-cooling unit. The air cooling system may include a non-refrigerant based cooling apparatus, for example a humidification unit, an evaporative cooling unit and/or an adiabatic cooling unit. Redundancy may be provided in the system by means of being designed for primary operation without refrigerant-based cooling. For example, the use of ambient air from outside the building can be used to cool the racks, provided that the temperature is below a maximum threshold temperature (for example 37 degrees Celsius). Use of ambient air, as the cooling air, can be sufficient (for example when utilising embodiments of the present invention in which ambient air is treated via a humidity-based cooling unit) for at least 97% of the duration of the operation of the data centre in certain climates. Thus, the 3% or less of the time where active refrigerant-based cooling is additionally required may be considered as an exceptional case, such that provision of a doubly redundant refrigerant-based active cooling system is rendered unnecessary. Thus, the data centre building may offer sufficiently robust and continuous operation without requiring two independent active refrigerant-based cooling systems (of the type requiring mechanical DX cooling, condensers, compressors, and the like).

The racks in the data centre may stand, preferably directly, on the floor. A row of racks may be provided at a discernible rack storage area. Each rack may be arranged to house a plurality of rack-mountable electronic components, such as IT components (for example server blades). Each rack may be in the form of a rack having a multiplicity of slots arranged in a single column. Each rack may have more than ten slots for insertion of separate IT equipment units. Each rack may have more than twenty such slots. Each row of racks may have ten or more racks in the row. Thus, each row of racks may, when operating at full capacity, accommodate over 200 separate equipment units, possibly more than 500. The data centre may have multiple rows and may for example have capacity to accommodate more than 1,000 separate items of IT equipment, for example computer servers, possibly more than 2,500.

The IT components in each rack may each be provided within a casing, for example a metal box. The casing may include one or more vents, for example grilles, at the front and rear of the casing to facilitate the flow of cooling air through the casing to cool the IT component during use. There may be one or more fans inside the casing. One or more racks may be housed in a cabinet. There may be one cabinet per rack. One cabinet may alternatively accommodate a plurality racks. The cabinet preferably has a vent or vents provided on its front face. The cabinet may have a vent or vents provided on its rear face.

Cabling may be held above or below the racks in cable ducts that run the length of the racks. The cable ducts are preferably provided above the racks. Cables may run from such cable ducts to IT equipment in the racks.

The data centre building may be a building in which all the interior space is taken up by the data centre. Of course, alternatively, the data centre building may be a building in which only part of the interior space is taken up by the data centre, with the rest of the interior space being available for other uses.

The racks may be already installed in the data centre building or, alternatively, the data centre building may be initially provided without racks. In such a case the racks will subsequently be installed in rack storage areas in the building. Each rack storage area is arranged to accommodate a plurality of racks (for example arranged in a single row) in which a plurality of rack-mountable electronic components may be housed. The rack storage areas may include fixings or other means on the floor for facilitating correct positioning of the racks when installed. Each cold aisle may be positioned adjacent to a rack storage area. Each hot aisle may be positioned adjacent to a rack storage area.

The present invention provides embodiments in which the data centre building is initially provided without the racks. In such a case there may for example be provided a data centre building (without racks) suitable for forming a data centre according to the above-described invention (with racks included). Such a data centre building may include one or more controllable air circulation systems. Such a data centre building may include one or more aisles comprising one or more cold aisles and/or one or more hot aisles. Such a data centre building may include one or more rows of rack storage areas, each row being arranged parallel to an aisle of the eventual data centre. The data centre building may be so arranged that, in use, when racks of IT equipment are installed in the data centre building to form a data centre, cooling air passes (for example under the control of the one or more controllable air circulation systems) from a cold aisle through the racks and/or through the racks to a hot aisle. The data centre building further includes an access door, for providing access to an aisle, the door being movable between an open position allowing personnel access to the aisle and a closed position. The door has an aperture, a controllable air intake arrangement accommodated in the aperture of the door, and the width of the door is wider than the width of the aisle associated with the door. The width of the aperture may thus be larger than, or substantially equal to, the width of the aisle.

It will of course be appreciated that the skilled person may be able, when considering a particular data centre building without racks installed therein, to discern which regions of the building would be deemed as the rack storage areas, as the hot aisles and as the cold aisles.

The present invention also provides a method of cooling electronic equipment in a data centre building. The method may comprise a step of providing and then operating a data centre building according to the present invention as described or claimed herein. The method may include a step of cooling items of electronic equipment, neighbouring an aisle, by transporting air via the controllable air intake arrangement accommodated in the aperture of a door associated with that aisle. It may be that items of electronic equipment are cooled by operating one or more air circulation devices to transport air above the floor to the racks in an aisle via such a controllable air intake arrangement. It may be that air is transported above the floor to the door, via the controllable air intake arrangement accommodated in the aperture of the door, then into a cold aisle. The method may include a step of cooling racks of items of electronic equipment by operating one or more air circulation devices to transport air above the floor via at least one access corridor, providing access to the racks. The method may include a step of removing air from the racks. The method may cause the removed air to be exhausted directly to the exterior of the building.

The one or more controllable air circulation systems may be arranged to cause circulation of cooling air to rack storage areas under a controlled pressure regime. An air circulation control unit may be provided to control such a process. Pressure sensors may for example be provided to provide a measure of pressure in different regions of the data centre. The control unit may be arranged to receive signals representative of the pressure so measured, such signals being used to control the cooling of the data centre. The cooling and/or the pressure regime may of course be adjusted by means of controlling (automatically) the controllable air intake of the access door arrangement mentioned above. The pressure regime may comprise maintaining differential pressures as between the pressure in a cold aisle and the pressure in a hot aisle, so that air flow is encouraged from the cold aisle to the hot aisle. The pressure regime may comprise maintaining differential pressures as between the pressure in a hot aisle and a downstream pressure, for example outside the building, to encourage extraction of air away from the hot aisle. The pressure regime may comprise maintaining differential pressures as between the pressure in a cold aisle and an upstream air duct or corridor. The differential pressure may be required upstream of a cold aisle simply to enable differential pressures downstream. The pressure differential between two successive points on the airflow route (for example either side of the racks or either side of an air intake dividing an aisle from an airflow) is preferably greater than 10 Pa, and preferably less than 100 Pa. It will be understood that ensuring that sufficient cooling air reaches each of the individual items of IT equipment may inevitably cause a certain pressure regime to be maintained. It may be that the controlled pressure regime is controlled by the one or more controllable air circulation systems by means of inputs from one or more air-flow sensors, for example velocity sensors, and possibly without the use of any conventional air-pressure sensors.

The IT equipment in the data centre will typically have a cooling requirement of at least 50 kW. The IT equipment in the data centre may have a cooling requirement of at least 100 kW, and possibly more than 200 kW. In some embodiments, the data centre may have a cooling requirement of greater than 300 kW. The method may extract heat at a rate of at least 5 kW per cold aisle, or optionally at a rate of at least 10 kW per cold aisle. When IT demand is high, there may be a need for higher heat extraction rates. The method may extract heat at a rate of at least 50 kW per cold aisle, and possibly at a rate of at least 80 kW per cold aisle. Such heat extraction rates may be achieved solely with ambient air cooling.

The method may include a step of cooling racks of items of electronic equipment by operating one or more air circulation devices to transport air from outside the building at ambient air temperature to the racks, preferably without utilising refrigerant-based active cooling. The air may then be removed from the racks and exhausted to outside the building via at least one air exhaust. The one or more air circulation devices may be provided upstream of the racks. The one or more air circulation devices preferably provide a sufficient pressure differential throughout the air flow path, to be able independently to flow at a rate of at least 10 $m^3s^{-1}$ per cold aisle (or optionally at least 8 $m^3s^{-1}$ per cold aisle, or optionally at least 5 $m^3s^{-1}$ per cold aisle). Such rates might represent the higher end of the likely range of operational air flow rates. The data centre building may be arranged to operate at low IT demand levels with air flow rates of the order of only 0.3 $m^3s^{-1}$ per cold aisle. In the case where there are for example, three or more (or optionally five or more) cold aisles in a building, or a floor thereof, air may be caused to flow at a rate of at least 50 $m^3s^{-1}$ through the building (or floor of the building, as the case may be), when operating at high demand for example. Alternatively or additionally, air may be caused to flow at a rate of at least 0.4 $m^3s^{-1}$ per rack. If there are 24 racks associated with a cold aisle, such a rate would be equivalent to about 10 $m^3s^{-1}$ per cold aisle. Alternatively or additionally, air may be caused to flow at a rate of at least 0.002 $m^3s^{-1}$ per occupied slot in the racks. If there are 40 racks associated with a cold aisle and 40 occupied slots per rack, such a rate would be equivalent to about 3.2 $m^3s^{-1}$ per cold aisle. Alternatively or additionally, air may be caused to flow at a rate of at least 0.005 $m^3s^{-1}$ per rack slot, preferably at a rate of at least 0.008 $m^3s^{-1}$ per rack slot. At low demand, the air may flow at a rate as little as 0.00024 $m^3s^{-1}$ per rack slot. If there are 24 racks associated with a cold aisle and 40 slots per rack (of which at any given time 10 or more are each closed over by a blanking strip thereby restricting or preventing the flow of air therethrough), such a rate may be equivalent to less than 0.2 $m^3s^{-1}$ per cold aisle. Air may be caused to flow at a rate of at least 0.01 $m^3s^{-1}$ per rack slot, or possibly at least 0.15 $m^3s^{-1}$ per rack slot (such rates again representing the higher end of the range of likely operational air flow rates). Thus, in an embodiment of the invention, a sufficiently large volume of air per second can be used to effect "ambient air" cooling of the IT equipment in the data room. There may therefore be less of a need for use of refrigerant-based active cooling. In certain embodiments of the invention, there is for example no need for CRAC units to be provided. This means of cooling may be used even when the ambient air temperature outside is higher than 20 degrees Celsius. Preferably, the method includes a step of operating the data centre and cooling it by means of airflows where the air flow rate is greater than 5 $m^3s^{-1}$ per cold aisle and also a step, performed at a different time, of operating the data centre and cooling it by means of airflows where the rate is less than 1 $m^3s^{-1}$ per cold aisle.

The present invention also provides a method of replacing a blade of a door, in the case where the door includes a bar extending horizontally across the door. In normal use the bar supports one or more the blades. The method of replacing the blade includes steps of removing at least part of the bar, removing the blade from the door whilst at least one other blade remains in position, and installing a replacement blade in place of the blade so removed. The part of the bar so removed may then be fitted back in place. It is not of course essential for the same part of the bar to be fitted back in place, if for example a spare part is available. As such, the method may include using an equivalent part (for example a spare part—or duplicate part) to replace the part of the bar so removed.

The door described above may have independent application for use within a building, not necessarily a data centre. Also, it will be appreciated that the door could be provided separately from the data centre building. The present invention thus further provides a door that is arranged to be fitted within a wall space, or door frame, the door being configured for use as the door of the invention as described or claimed herein. The door may thus be sized to allow human access therethrough and may comprise a controllable air intake arranged such that the flow of air through the door, when in its closed position, is controllable by means of the controllable air intake. The door will have an aperture in which is mounted such a controllable air intake arrangement. The door is preferably arranged to receive a control signal for controlling the operation of a motor provided to move the controllable air intake. The door may be wider than 1.2 m, that being a typical aisle width for a data centre. The width of the aperture is preferably greater than 1 m, and may be about 1.2 m wide. The controllable air intake may comprise a plurality of blades all arranged to rotate about parallel axes. The blades may comprise at least one pair of adjacent blades that are arranged to rotate simultaneously in opposite directions. Other features mentioned above may be incorporated into this aspect of the invention.

There is also provided a kit of parts for constructing a data centre, or part thereof, for example in a space within a building. The kit includes one or more elements that cooperate to define an aisle width. The kit also includes a door according to the invention as described or claimed herein, the door having a width greater than the aisle width. The elements may include one or more structures that define the location of the cold aisle. The elements may include one or more structures that define the location of the hot aisle. The elements may include one or more structures that define the location of the racks. The structures may include one or more panels, for example, blanking panels. The structures may include one or more partitions arranged for installation in a space within a building.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention will now be described, by way of example only, with reference to the accompanying schematic drawings, of which.

DETAILED DESCRIPTION

Figure 1:
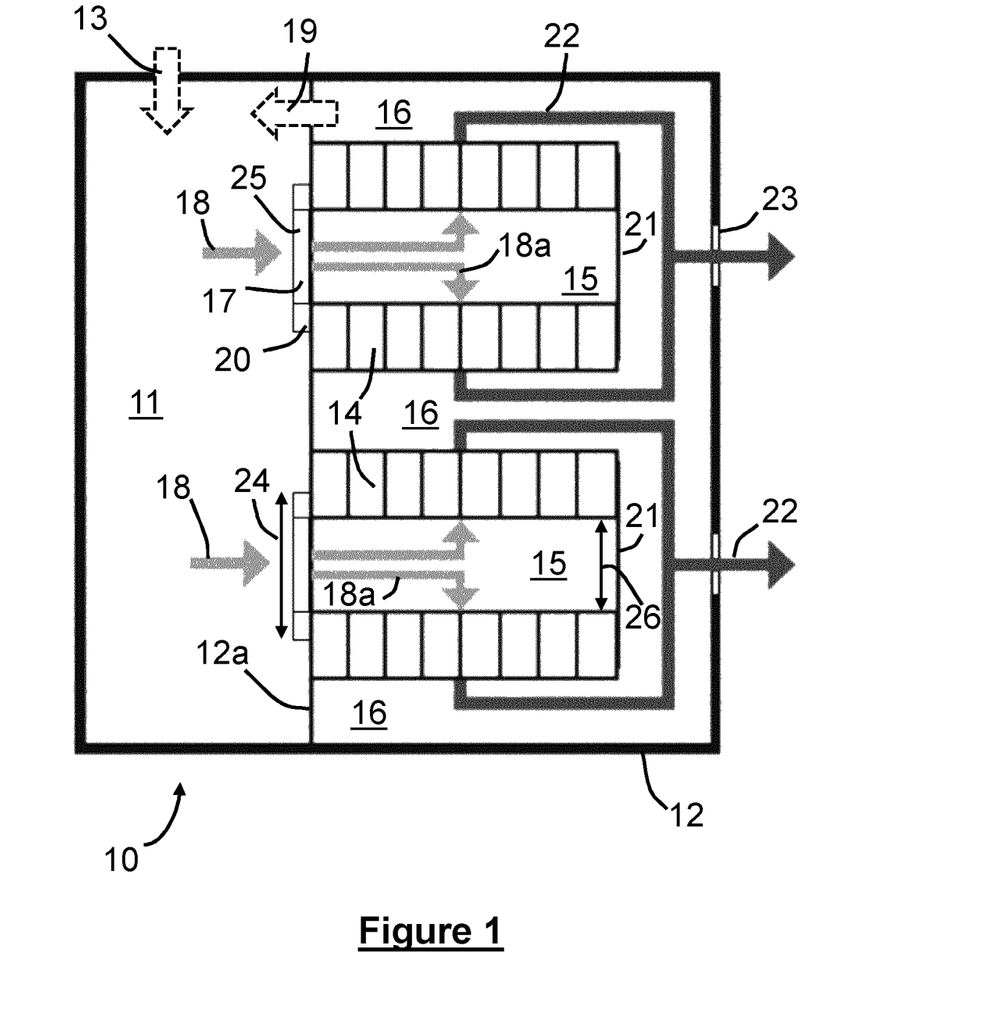
FIG. 1 shows a data centre building according to a first embodiment of the invention having a single closed aisle.

FIG. 1 shows a data centre building 10 according to a first embodiment of the invention. The building 10 is rectangular with external walls 12. The building is divided into front and rear sections by an internal dividing wall 12a. The front section (on the right in FIG. 1) of the building 10 comprises four rows of racks 14. The racks 14 extend away from the internal dividing wall 12a, towards the front of the building. Although only shown schematically in FIG. 1, each rack in each row is in the form of an open fronted 42u standard universally compatible server rack. There are 20 such racks in each row, each rack typically housing up to 40 items of IT equipment (typically server blades). There may therefore be as many as 3,200 items of IT equipment in the racks in the building 10. A blanking panel 21 extends between the front ends of the first pair of rows of racks, thereby defining a cold aisle 15. A further blanking panel 21 extends between the front ends of the second pair of rows of racks, thereby defining a further cold aisle 15. The cold aisles 15 may be considered as being encapsulated cold aisles. A hot aisle 16 is defined between the two cold aisles. The aisles between the racks 14 and the external wall 12 may also be considered as hot aisles 16. At the end of each cold aisle opposite the blanking panel 21 there is a door 20 that permits personnel access into the cold aisle. The doors 20 open and close over doorways formed in the internal dividing wall 12a. Each door has an aperture 25 in which a controllable vent system 17 is housed to allow and control the flow of air into the cold aisle 15 when the door 20 is closed.

The rear section (on the left in FIG. 1) houses an air optimiser unit 11, which provides a system of circulating cooling air in the building 10. Cooling air 18 is produced by the air optimiser unit 11 using ambient air from outside the building (shown schematically by arrow 13) and/or air recirculated from within the building (shown schematically by arrow 19). The amount of ambient air 13 used, if any, and the amount of recirculated air 19, if any, used by the air optimiser unit 11 is selected by the air optimiser 11 in dependence on the outside air conditions (temperature and humidity). For example, if the ambient air outside the building 10 is sufficiently cool, the ambient air may be used as cooling air, without requiring any active cooling by the air optimiser unit 11. If additional cooling of the air is required, the air optimiser unit 11 employs adiabatic cooling with humidifiers and/or mechanical cooling with DX cooling units as required. The cooling methodology employed may be as set out in International Patent Application No. PCT/GB2011/050987, the contents of which are hereby incorporated by reference thereto. The air optimiser unit 11 includes a bank of fans (not shown in FIG. 1) for pushing air through the building 10. The amount of cooling air 18a admitted into each cold aisle is regulated, under the control of the air optimiser unit 11, by the controllable vents 17 so that the right amount of cooling air is supplied to each cold aisle to adequately cool the IT equipment in the racks 14. The hot air (shown by darker arrows 22) from the hot aisles 16 may be exhausted via controllable vents 23 and/or recirculated (arrow 19). It will be seen that the width 24 of each door 20 is greater than the width 26 of each cold aisle 15. The aperture 25 in the door 20 in which the vents 17 are mounted may therefore be of a width that is substantially the same as the width of the cold aisle 15.

As mentioned above, air is cooled/treated as necessary in the air optimiser unit 11 resulting in cooling air 18a, which enters the cold aisles 15, via the vents 17. The cooling air 18a moves over the racks 14 to reach the hot aisles 16 and in the process cools the IT equipment in the racks 14. The resulting hot air 22 coming off the racks 14 is carried away. It will of course be appreciated that the hot air 22 is simply the result of the cooling air 18a having been heated by the equipment in the racks 14 and is otherwise essentially the same air. As such, the operation may be considered as involving the flow of cooling air into the cold aisles 15, the flow of cooling air via the racks 14 and then the flow of cooling air (then heated by the racks such that the "cooling air" may then have less, if any, ability to cool) into and then out of the hot aisles. As such "hot air" or "exhaust air" can be considered as heated or used "cooling air". In the Figures air upstream of the racks is indicated by light arrows and downstream or exhaust air is indicated by dark arrows. The air for cooling the racks travels above floor all the way from the air optimiser unit 11 to the racks 14 and away from the racks 14.

The air optimisation unit 11 contains various other air treatment apparatus (not shown in the Figures), including for example air filters and sound attenuation apparatus, and a control unit for managing the cooling of the IT racks. In use the control unit receives data from various sensors including sensors inside and/or outside the data centre for measuring air temperature and/or air humidity. It uses this information to control the fans, humidification apparatus, cooling system and controllable vents in the building (including the vents in the doors) in order to achieve effective cooling of the IT equipment in the IT racks. The control unit may also receive data from one or more air pressure sensors and/or one or more air-flow sensors and control the vents and/or fans so that a desired air pressure regime can be achieved. For example, it may be that the pressure differential between the cooling air and the hot air is maintained at a sufficient level to ensure there is no return of hot air through the racks. This can be done by monitoring air flow rates using air flow sensors and/or measure air pressure at various locations throughout the date centre.

Cables are run vertically to the top of the racks through cable management panels and guided through cable trays (not shown) at the top of the racks. Cables can then be run down one side of the row of racks in a cable tray. Hence, the cable is kept out of the air flow and this improves efficiency.

Figure 2:
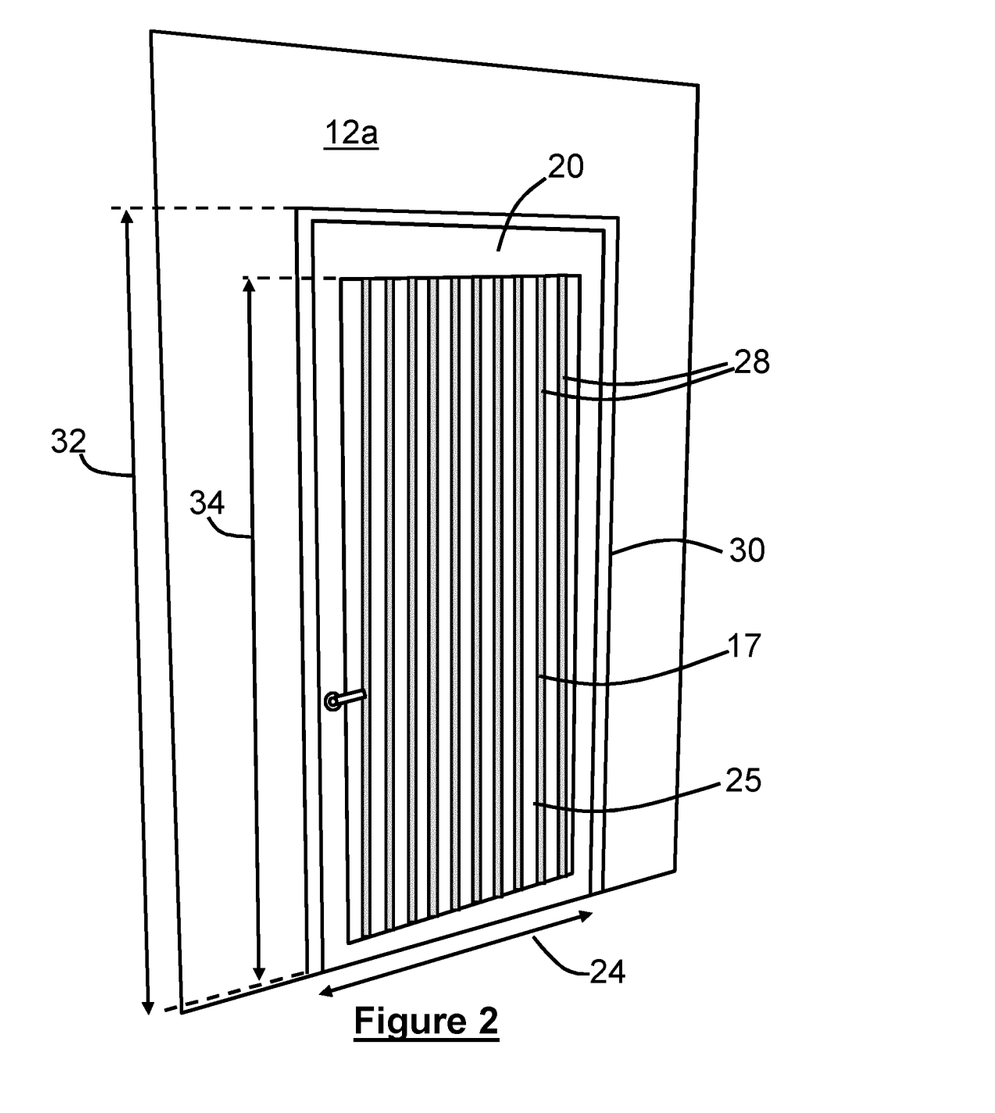
FIG. 2 is a view showing a door with a variable air flow intake as used in the first embodiment, the door being shown in a position closing off a doorway into the cold aisle.
Figure 3:
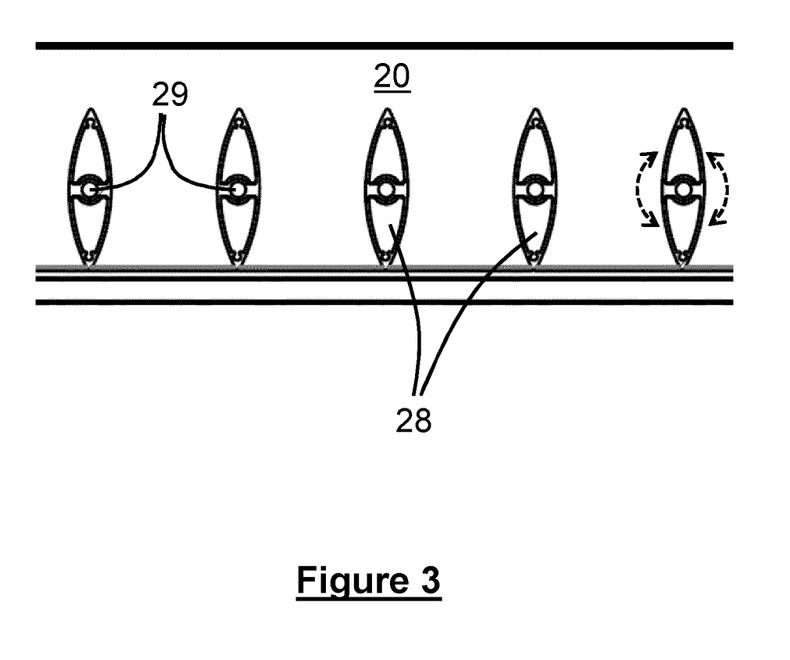
FIG. 3 shows a partial cross-section of the door shown in FIG. 2.

FIG. 2 shows one of the doors 20 that allows personnel access to the cold aisle whilst also providing a means for controlling airflow through the door, whilst the door is in its closed position. The door 20 is shown in this closed position, in which it closes over the doorway to the cold aisle. The door 20 includes an adjustable air intake means in the form of a vent 17 having a number of vertical blades 28 arranged in a row. FIG. 3 shows a cross-section taken across a part of the width of the door, showing five blades 28 in cross-section. The blades are each mounted for rotation about a vertical axis 29, such that the vent may be moved between closed and open positions by means of rotation of the blades. FIG. 2 shows the blades 28 near to the fully open state. The blades 28 are arranged such that pairs of adjacent blades are arranged to rotate simultaneously in opposite directions. Having such an arrangement facilitates better control of the air-flow in comparison to the case where all blades rotate in the same direction. Two motors (not shown) are arranged to move the blades 28, one motor for the odd-numbered blades and one motor for the even-numbered blades (counting from left to right). (It will be appreciated that one motor could be arranged to control all the blades.) The width 24 of the door is 1.2 m. The height 32 of the door is 2.4 m. The area of the door is therefore about 2.9 $m^2$. The aperture 25 in which the blades are mounted has a width of 1 m and a height of 2 m. The area of the aperture is therefore about 2.0 $m^2$. The aperture thus extends across more than 80% of the width of the door and more than 80% of the height of the door. The effective open area when the vent 17 is fully open is about 1.6 $m^2$. The vent is arranged such that in the event of a failure the vent fails "open".

The door arrangement includes a flexible cable (not shown in FIG. 2) that runs from the motors to the hinge side 30 of the door and then onto the structure of the adjacent wall 12a. The cable carries a control signal which controls the operation of the motors. The control signal is set in dependence on the level of cooling air demand by the IT equipment supplied by the cold aisle associated with the door, as compared for example to the demand by the IT equipment supplied by other cold aisles. Where the cold aisles have different cooling demands placed on the them, the vents of the door of the aisle that has the greatest demand will typically be fully open whereas the vents of the other doors may be partially open (if their cooling demand is significantly less). The fans operate at the appropriate level to supply cooling air to all of the cold aisles at a flow rate sufficient to meet the total demand.

Figure 4:
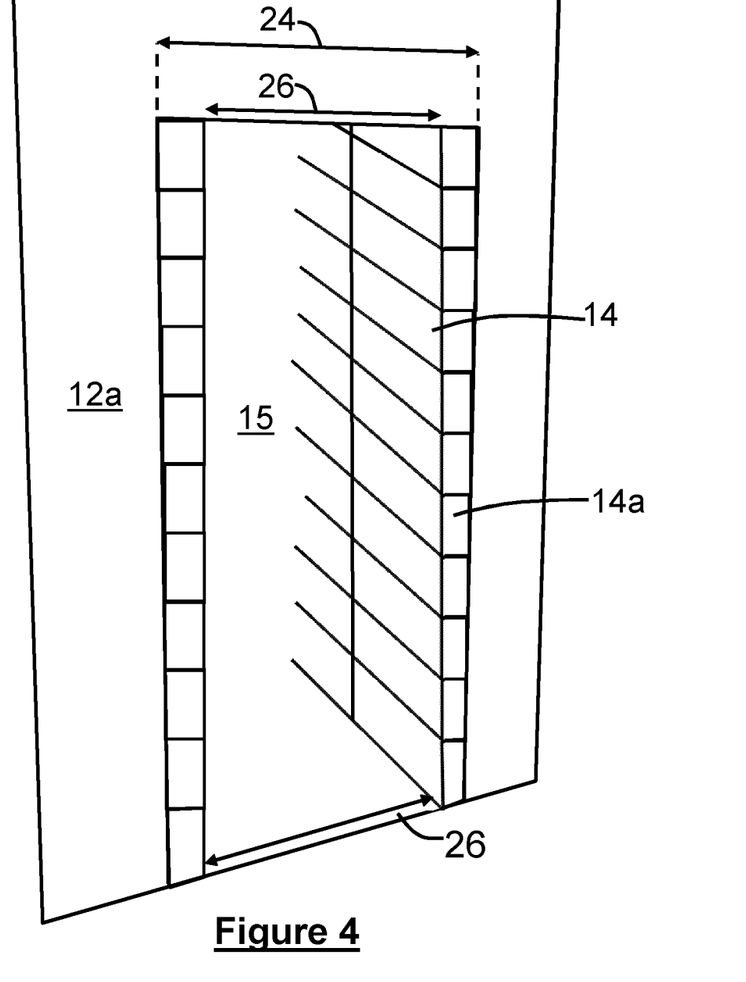
FIG. 4 is the same view as FIG. 2, but with the door removed so as to reveal the doorway and the cold aisle.

FIG. 4 shows the doorway and cold aisle 15 when the door 20 is open (the door has been omitted from FIG. 4 for the sake of clarity). The aisle has a width 26 of 1.0 m. It will be seen that the width 24 of the doorway (and that of the door therefore) is wider than the aisle. The fronts of the racks 14 thus intrude into the doorway when the door is open. However, the aperture 25 of the venting arrangement of the door when the door is closed has a width that is about the same as the width of the aisle. The flow of air via the aperture when the vents are fully open is not therefore subject to any significant constriction as compared to its passage down the cold aisle. The velocity of air as it enters the cold aisle (i.e. near the door) is not therefore significantly faster than the velocity of air further down the cold aisle. The supply of cooling air to the racks 14a by the door is not therefore adversely affected (as it might be if the velocity of cooling air were significantly higher).

Figure 5:
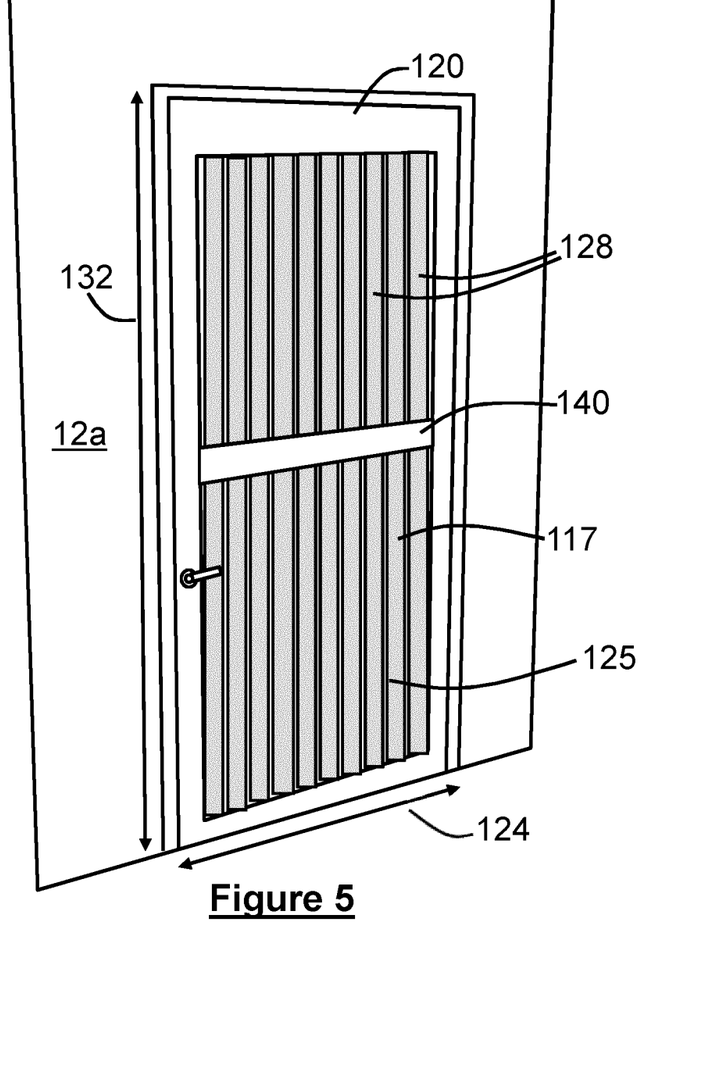
FIG. 5 shows a door with a variable air flow intake according to a second embodiment1

FIG. 5 shows a door 120 according to a second embodiment, which is similar to that shown in FIG. 2, but is slightly larger and further includes a bar 140 for supporting the blades 128 of the venting arrangement 117. The door 120 of FIG. 5 also allows personnel access to the cold aisle whilst also providing a means for controlling airflow through the door, whilst the door is in its closed position (the position shown in FIG. 5). The door 120 includes a controllable vent arrangement 117 having a number of vertical blades 128 arranged in a row. The blades 128 are each mounted for rotation about a vertical axis, such that the vent may be moved between closed and open positions by means of rotation of the blades. FIG. 5 shows the blades 128 closer to the closed state (by way of a comparison with FIG. 2). The differences between the door of FIG. 5, as compared to the door of FIG. 2, will now be described. In this embodiment, the width 124 of the door is 1.4 m and the width of the aperture 125 in which the blades are mounted is 1.18 m. This is substantially the same as the width of the cold aisle, which in this case, is 1.20 m. (It will be appreciated that in this embodiment the width of the aisle is the same as the width of the aperture, to within +1-2%, and that therefore the two widths may be considered as being substantially the same width.) The height 132 of the door is 2.9 m. The area of the door is therefore about 4 $m^2$. The aperture 125 in which the blades are mounted has a height of 2.6 m. The area of the aperture 125 is therefore about 3.1 $m^2$. The provision of the central bar 140 assists with giving structural rigidity to the blades, preventing chatter during use, and with keeping the blades in place. In this embodiment, each blade is provided in two parts which connect end-to-end via a shaft, which passes through an aperture (not visible in FIG. 5) formed in the central bar 140. The bar 140 is formed from two main parts (a front part and a rear part) which split the bar along its length. The two parts cooperate to form the apertures in which the shafts of the blades 128 are held during use. If a vent blade 128 needs to be replaced, the bar 140 is removed by detaching the front part of the bar 140 from the rear part of the bar. The top part of the blade is held in position, by means of a grub screw, on a gear that in use enables the motor to cause the rotation of the blade. This grub screw us unscrewed to release the top part of the blade. The bottom part of the blade rests on a bearing in the bottom of the door under its own weight. With the split bar 140 in its disconnected state and the top grub screw released, there is enough flexibility to allow an entire single blade to be removed, separately from the other blades and without needing to disassemble any other parts of the door.

Figure 6:
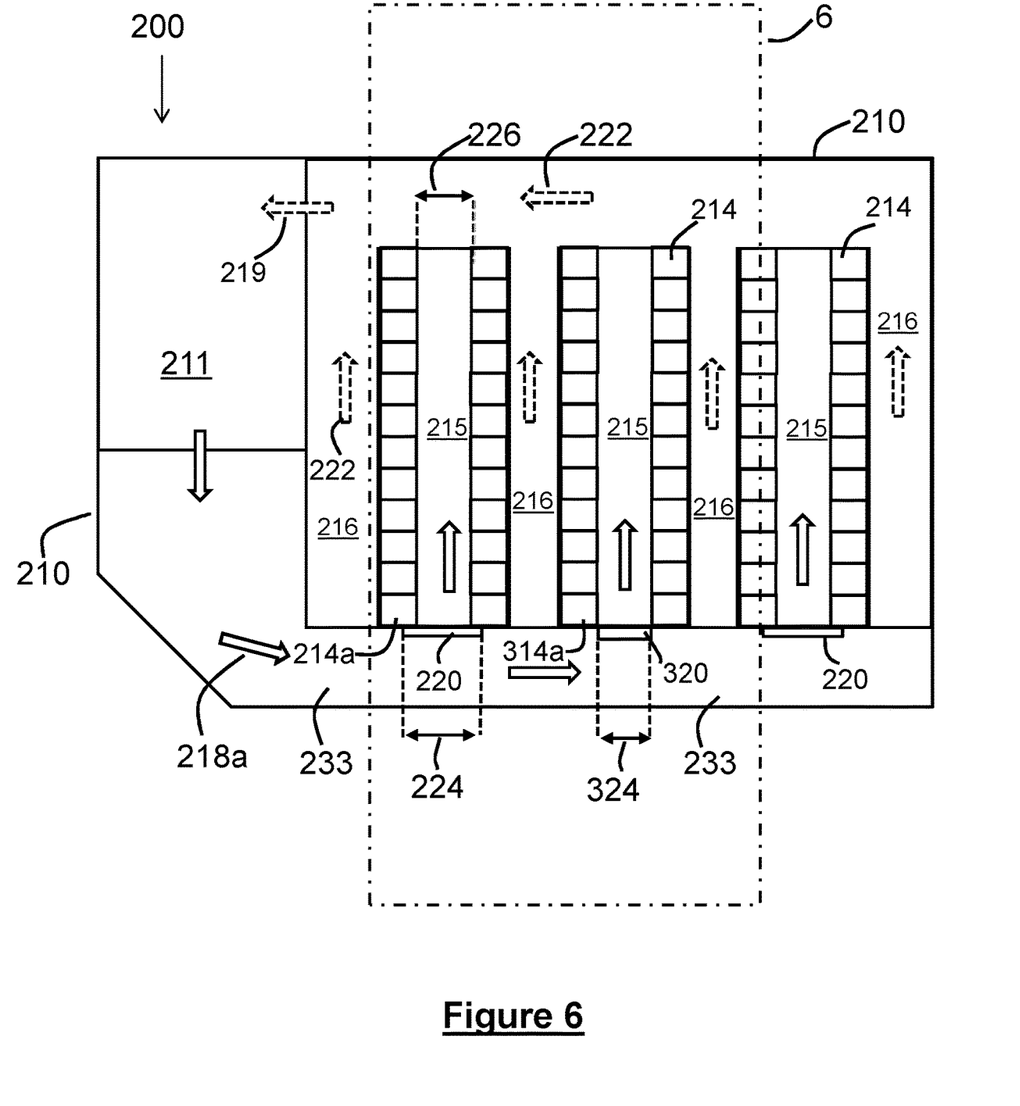
FIG. 6 is a plan hybrid view of both a data centre building according to a third embodiment and a data centre building according to the prior art.
Figure 7:
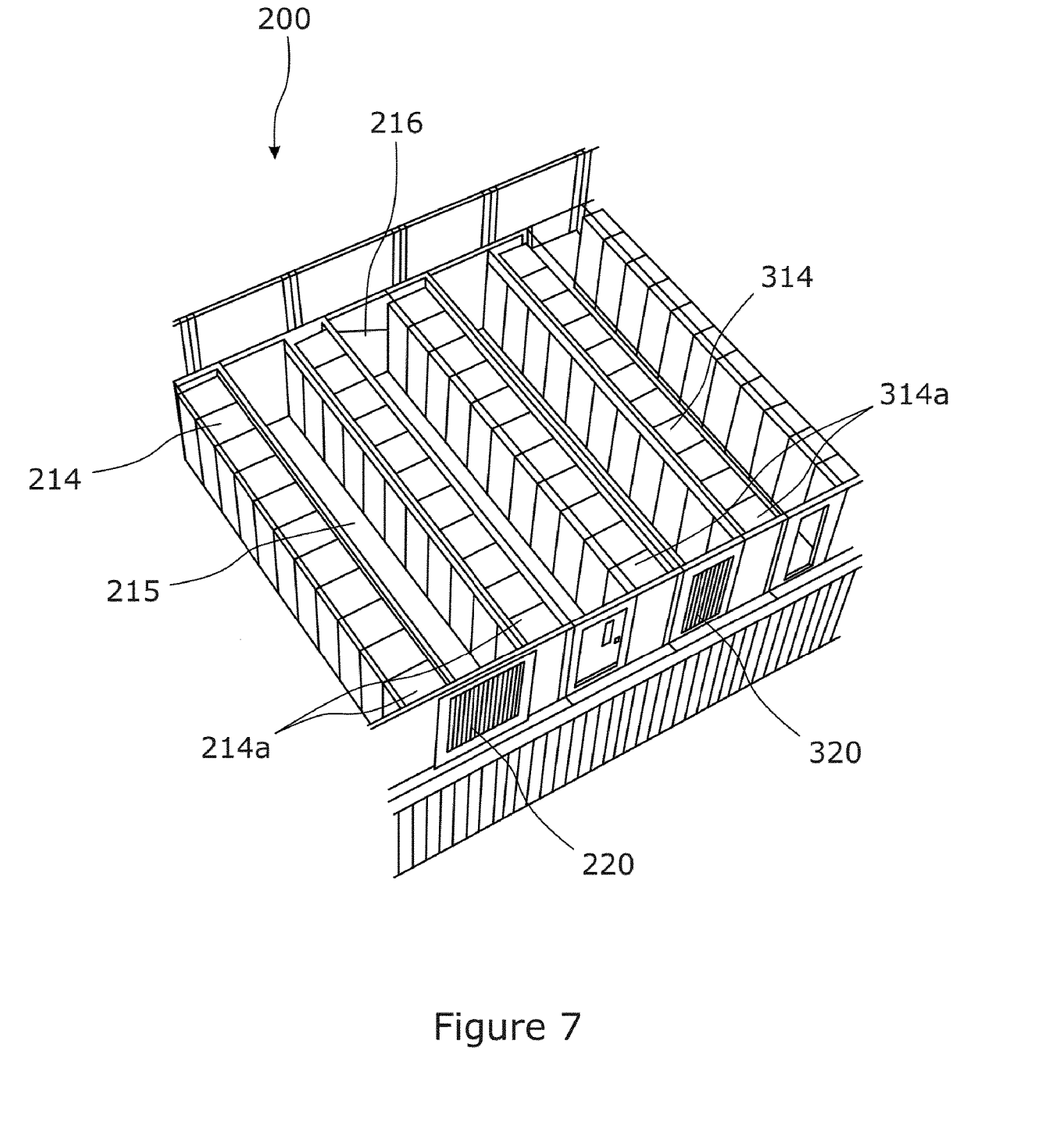
FIG. 7 is a perspective view of part of the data centre buildings shown in FIG. 6.

FIGS. 6 and 7 are hybrid views showing both (i) a rectangular data centre building 200 according to a third embodiment and (ii) a cold-aisle vented-door of the prior art to aid understanding. With reference to FIG. 6, there is shown a data centre building 200 having external walls 210 and which uses an indirect air cooling method for cooling the computer servers housed in the racks 214.

The IT racks 214 define three cold aisles 215 interleaved between four hot aisles 216. The cold aisles 215 are served with cooling air supplied by the indirect air optimiser unit 211 via a cold air corridor 233. The cooling air 218a enters each cold aisle 215, via the vents in the door 220 associated with that aisle. The cooling air 218a passes via the racks 214 to the hot aisles 216 and in the process cools the IT equipment in the racks 214. The resulting hot air 222 is then fed back to the air optimiser unit 211 as recirculated air 219. The received air 219 from the hot aisles 216 is cooled by means of a heat exchange system (not shown) of the indirect air optimiser unit 211 to produce the cooling air 218a that is then again supplied to the cold air corridor 233. The cooling air for cooling the racks travels above floor all the way from the air optimiser unit 211 to the racks and away from the racks. The heat exchange system and the indirect air optimiser may operate in the same way as that of the apparatus described and claimed in International Patent Application No. PCT/EP2016/064626, the contents of which are hereby incorporated by reference thereto. In FIG. 6, the door arrangement 320 for the middle cold aisle is one similar to that of the prior art. The door 220 to the leftmost cold aisle is in accordance with a third embodiment of the present invention. FIG. 7 shows as a cut-away perspective view the portion of FIG. 6 marked by the box 6. It will be seem that the door 320 of the prior art has a width that is about the same as the width of the cold aisle, namely about 1.2 m. The aperture of the door 320 of the prior art, being about 1.0 m, therefore has a width that is significantly less than the width of the cold aisle 315 (being less than 90% of the width of the aisle). Having a narrower aperture than the width of the aisle presents a pinch point (or constriction) to the incoming airflow. This pinch point acts to accelerate the air as it passes through the aperture in the door even when the vent arrangement is fully open. Under certain operating conditions this could possibly result in uneven distribution of cooling air as compared between (a) the amount of air delivered to the fronts of the racks 314a in the immediate vicinity of the door 320 and (b) the amount of air delivered to the fronts of the racks 314 further downstream. By way of contrast, the door 220 of the embodiment of the invention has a width that is about 15% wider than the width of the cold aisle. The aperture of the door 220 is thus able to have a width that is about the same as the width of the cold aisle 215. Air can therefore move via the doorway, when the vents are fully open, without experiencing any significant acceleration or pinch point. Cooling air is thus able to be delivered evenly as between the racks 214a in the immediate vicinity of the door 320 and those racks 314 further downstream.

The cold aisles, hot aisles, cold corridor and the space downstream of the hot aisles (a hot corridor) may each allow personnel access. For example, the aisles/corridors may be provided with a flat floor, provide a width of at least 1 m (preferably more) for their entire length, have a height of at least 2 m, and be adequately lit.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

There may be further controllable vents not being provided in the doors. For example, there may be one or more air intake damper arrangements for controllably admitting ambient air from outside. There may be one or more air exhaust damper arrangements for controllably exhausting air to the outside. As already mentioned above, there may also be one or more air recirculation damper arrangements for controllably recirculating at least some of the air that has been heated by means of direct and/or indirect heating by the IT equipment in the racks.

The data centre may include a separate plant room which may or may not be provided in the same general space as the air optimisation unit. The plant room may for example accommodate fire suppression gas equipment, one or more control panels, and an uninterruptable power supply and back-up batteries.

The layout of the racks, and/or the construction of the building, may be as set out in International Patent Application Nos PCT/GB2010/000759 or PCT/GB2012/051894, the contents of which are incorporated herein by reference thereto. For example, the embodiments could be adapted to work in a multi-storey data centre building.

The air may be supplied at least partially via an underfloor duct.

Cooling air may be transported via one or more apertures or passageways in data centre that are not arranged to permit personnel access.

The racks and aisles defined by the racks need not be straight and/or rectangular in plan-view.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A data centre including
one or more controllable air circulation systems,
one or more aisles comprising a plurality of cold aisles interleaved between at least three hot aisles,
a plurality of rows of racks, each row being arranged parallel to at least one of the aisles, the data centre being so arranged that in use cooling air passes, under the control of the one or more controllable air circulation systems, from a cold aisle through the racks and/or through the racks to a hot aisle, and
an access door providing access to at least one of the aisles, the door being movable between an open position allowing personnel access to the aisle and a closed position,
wherein
each cold aisle is defined between two adjacent rows of racks,
each cold aisle has a width that is substantially constant along its length,
the door has an aperture,
the one or more controllable air circulation systems comprises a controllable air intake arrangement accommodated in the aperture of the door,
the width of the door is wider than the width of the aisle associated with the door, and
the width of the aperture is larger than or substantially equal to the width of the aisle,
the access door is one of multiple such doors, each door providing access to a respective cold aisle,
there is provided a cold air supply region for transporting, under the control of the one or more air circulation systems, cooling air, above the floor, via the respective doors to the respective cold aisles,
the cold air supply region has a height greater than 1.5 m above the floor.

2. A data centre according to claim 1, wherein the air intake arrangement is configured to be movable to any one of at least five different positions, each position corresponding to a different level of openness.

3. A data centre according to claim 2, wherein the controllable air intake arrangement comprises a row of vertical blades arranged for rotation about a vertical axis, such that the air intake arrangement may be moved between closed and open positions by means of rotation of the blades.

4. A data centre according to claim 3, wherein the blades extend across more than 70% of the width of the door.

5. A data centre according to claim 4, wherein a bar extends horizontally across the door and supports one or more the blades, the bar being vertically positioned in the region between 20% and 80% of the height of the aperture.

6. A data centre according to claim 5, wherein the blades extend across more than 80% of the height of the door.

7. A data centre according to claim 4, wherein the blades extend across more than 80% of the height of the door.

8. A data centre according to claim 3, wherein a bar extends horizontally across the door and supports one or more the blades, the bar being vertically positioned in the region between 20% and 80% of the height of the aperture.

9. A data centre according to claim 8, wherein the blades extend across more than 80% of the height of the door.

10. A data centre according to claim 3, wherein the blades extend across more than 80% of the height of the door.

11. A data centre according to claim 1, wherein the controllable air intake arrangement comprises a row of vertical blades arranged for rotation about a vertical axis, such that the air intake arrangement may be moved between closed and open positions by means of rotation of the blades.

12. A data centre according to claim 11, wherein the blades extend across more than 70% of the width of the door.

13. A data centre according to claim 12, wherein a bar extends horizontally across the door and supports one or more the blades, the bar being vertically positioned in the region between 20% and 80% of the height of the aperture.

14. A data centre according to claim 13, wherein the blades extend across more than 80% of the height of the door.

15. A data centre according to claim 12, wherein the blades extend across more than 80% of the height of the door.

16. A data centre according to claim 11, wherein a bar extends horizontally across the door and supports one or more the blades, the bar being vertically positioned in the region between 20% and 80% of the height of the aperture.

17. A data centre according to claim 16, wherein the blades extend across more than 80% of the height of the door.

18. A data centre according to claim 11, wherein the blades extend across more than 80% of the height of the door.

19. A data centre building suitable for forming a data centre according to claim 1, wherein the data centre building includes
   one or more controllable air circulation systems,
   one or more aisles comprising a plurality of cold aisles interleaved between at least three hot aisles,
   a plurality of rows of rack storage areas, each row being arranged parallel to at least one of the aisles, the data centre building being so arranged that, in use, when racks of IT equipment are installed in the data centre building to form a data centre, cooling air passes, under the control of the one or more controllable air circulation systems, from a cold aisle through the racks and/or through the racks to a hot aisle, and
   an access door providing access to at least one of the aisles, the door being movable between an open position allowing personnel access to the aisle and a closed position,
   wherein
   each cold aisle is defined between two adjacent rows of rack storage areas,
   each cold aisle has a width that is substantially constant along its length,
   the door has an aperture,
   the one or more controllable air circulation systems comprises a controllable air intake arrangement accommodated in the aperture of the door,
   the width of the door is wider than the width of the aisle associated with the door, and
   the width of the aperture is larger than or substantially equal to the width of the aisle,
   the access door is one of multiple such doors, each door providing access to a respective cold aisle,
   there is provided a cold air supply region for transporting, under the control of the one or more air circulation systems, cooling air, above the floor, via the respective doors to the respective cold aisles,
   the cold air supply region has a height greater than 1.5 m above the floor.

20. A method of cooling electronic equipment in a data centre according to claim 1, wherein the method comprises the steps of:
   cooling items of electronic equipment by operating the one or more air circulation devices to transport air above the floor to the racks in an aisle via the controllable air intake arrangement accommodated in the aperture of a door associated with that aisle.

21. A method of cooling electronic equipment according to claim 20, wherein air is transported above the floor to the door, via the controllable air intake arrangement accommodated in the aperture of the door, then into a cold aisle.

* * * * *